(12) United States Patent
Frankel

(10) Patent No.: US 8,432,546 B2
(45) Date of Patent: *Apr. 30, 2013

(54) METHOD AND SYSTEM FOR STIMULATED RAMAN MICROSCOPY BEYOND THE DIFFRACTION LIMIT

(76) Inventor: Robert D Frankel, Rochester, NY (US)

( * ) Notice: Subject to any disclaimer, the term of this patent is extended or adjusted under 35 U.S.C. 154(b) by 540 days.

This patent is subject to a terminal disclaimer.

(21) Appl. No.: 12/726,829

(22) Filed: Mar. 18, 2010

(65) Prior Publication Data

US 2010/0238438 A1    Sep. 23, 2010

Related U.S. Application Data

(60) Provisional application No. 61/161,262, filed on Mar. 18, 2009.

(51) Int. Cl.
*G01J 3/28* (2006.01)

(52) U.S. Cl.
USPC .......................................................... 356/328

(58) Field of Classification Search .......... 356/326–328, 356/456, 451
See application file for complete search history.

(56) References Cited

U.S. PATENT DOCUMENTS

| | | | |
|---|---|---|---|
| 5,034,613 A | 7/1991 | Denk et al. | |
| 6,844,963 B2 * | 1/2005 | Iketaki et al. | 359/368 |
| 7,106,436 B1 * | 9/2006 | Gord et al. | 356/301 |
| 7,755,063 B2 * | 7/2010 | Baer | 250/458.1 |
| 2009/0046298 A1 * | 2/2009 | Betzig | 356/521 |
| 2012/0069332 A1 * | 3/2012 | Frankel | 356/301 |

OTHER PUBLICATIONS

Betzig et al., "Imaging Intracellular Fluorescent Proteins at Nanometer Resolution", Science, 313:1642-1645 (2006).

Cheng et al., "Theoretical and experimental characterization of coherent anti-Stokes Raman scattering microscopy", Optical Society of America B, 19(6):1363-1375 (2002).

Freudiger et al., "Label-free biomedical imaging with high sensitivity by stimulated Raman scattering microscopy", Science, 322:1857-1861 (2008).

Klar et al., "Subdiffraction resolution in far-field fluorescence microscopy", Optics Letters, 24(14):954-956 (1999).

Potma et al., "Chemical imaging of photoresists with coherent anti-Stkes Raman scattering (CARS)", J. Phys. Chem. B, 108(4):1296-1301 (2004).

Rust et al., "Sub-diffraction-limit imaging by stochastic optical reconstruction microscopy (STORM)", Nature Methods, 3:793-796 (2006).

Willig et al., "STED microscopy reveals that synaptotagmin remains clustered after synaptic vesicle exocytosis", Nature, 400:935-939 (2006).

* cited by examiner

*Primary Examiner* — Kara E Geisel
(74) *Attorney, Agent, or Firm* — Henry M. Feiereisen LLC

(57) ABSTRACT

Systems and methods for probing a Raman signature of a sample with a resolution exceeding the diffraction limit are described. These systems, called GASSE (Gain Saturated Stimulated Emission) and iGASSE (interferometric GASSE), are detecting a Raman signal produced in a sample located at the focal spot of a Gaussian pump pulse. Two additional pulsed laser beams (Stokes beams), a central Stokes beam having a Gaussian beam profile and another Stokes beam having an annular beam profile, are also focused to the focal spot. The spatial and temporal phases of the laser pulses are adjusted to produce destructive interference over most of the temporal width of Stokes pulses, which causes emission from the central Stokes beam to narrow well below the diffraction limit. A two-dimensional image of the sample is produced by scanning the combined beams across the sample. The system may find applications in biomedical and semiconductor technology.

18 Claims, 8 Drawing Sheets

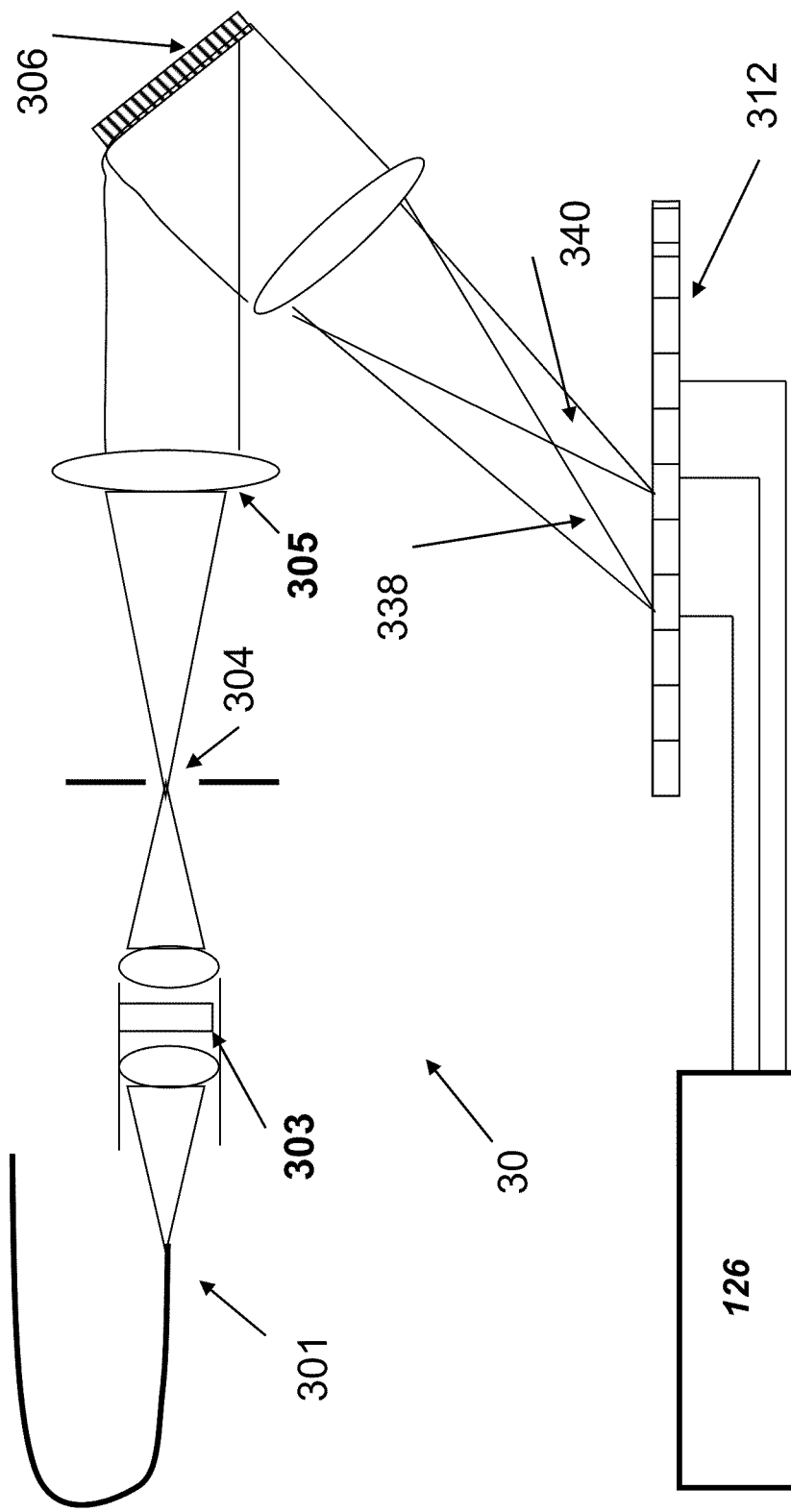

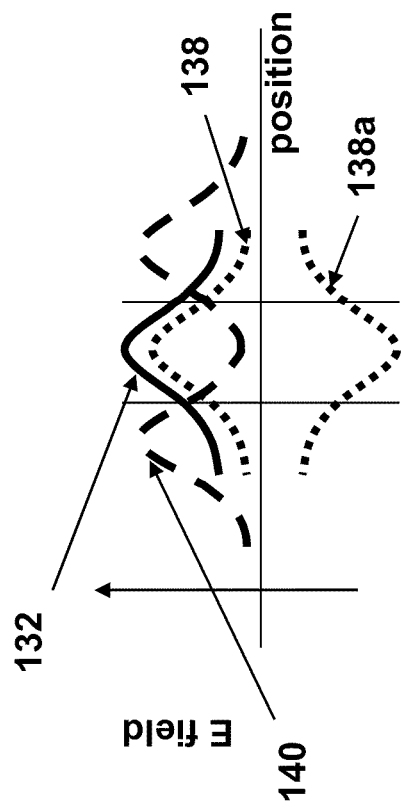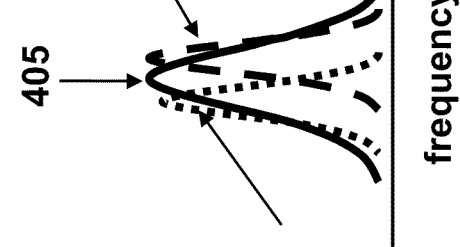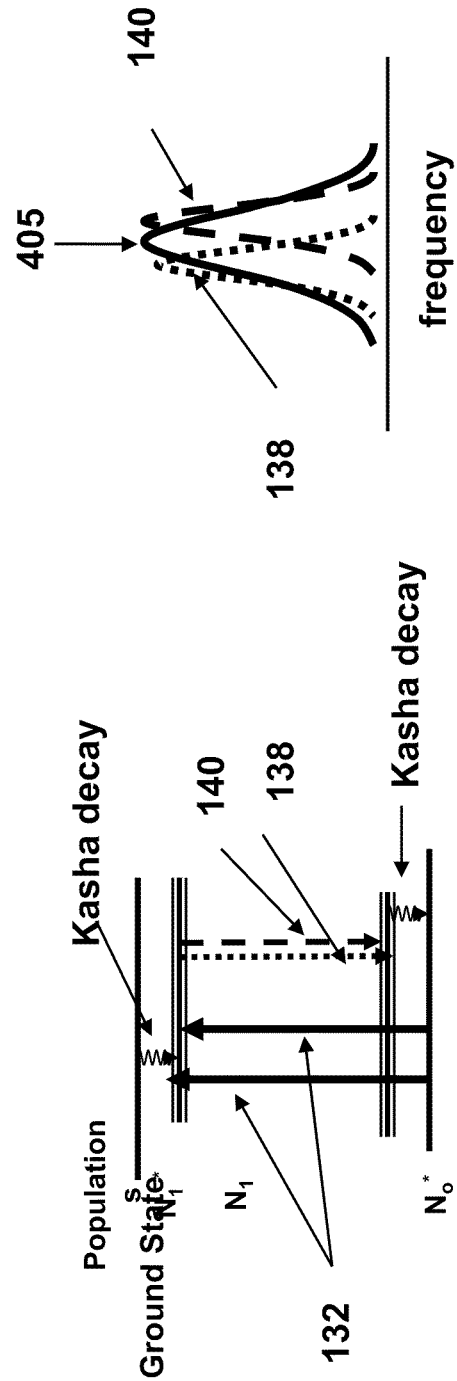

METHOD AND SYSTEM FOR STIMULATED RAMAN MICROSCOPY BEYOND THE DIFFRACTION LIMIT

FIELD OF INVENTION

This invention relates to the field of Raman and fluorescence microscopy, and more particularly to the field of stimulated Raman and stimulated fluorescence microscopy to image the presence of specific molecular bonds to identify molecules with a resolution beyond the diffraction limit.

BACKGROUND TO THE INVENTION

The resolution limit in traditional optical microscopy is limited by the numerical aperture of the microscope (NA) and the wavelength $\lambda$ of imaging light, generally referred to as Raleigh limit or diffraction limit; and is equal to $0.61(NA)\lambda$. This limit has recently been overcome in the case of fluorescence microscopy with Stimulated Emission Depletion (STED) microscopy by applying the statistical localization techniques of Photo Activation Localization Microscopy (PALM) and STochastic Optical Reconstruction Microscopy (STORM). These techniques are based on the physics of incoherently driven optical fluorescent transitions in dyes or other fluorescent molecules. In these techniques, light of one color turns off a fluorescent molecule, while light of another color is used to photo-stimulate the release of fluorescent photons producing an image of the molecules.

In STED microscopy, a first focused circular pulsed laser beam is used to provide an excited electronic state in fluorescent molecules at the focus of a microscope objective. Then a second pulsed laser beam of a different wavelength, focused to an annular shape is used to cause stimulated emission from the excited molecules in the annular spot de-excite the molecules back to the ground state manifold of the molecule. The annular beam is of the same size as the first beam but with a zero in the electric field at the center of the annulus of the stimulating beam. Unfortunately, this technique depends on the presence of efficient fluorescent molecules, where the fluorescence is often provided by a label rather than the intrinsic molecules. However, this technique is unable to identify intrinsic molecules that are not strongly fluorescent.

PALM and STORM work by turning off and on fluorescent emission from isolated dye molecules and finding the center position of the peak of emission of individual fluorescent molecules. These two techniques work best with a low concentration of fluorescent molecules.

Since not all molecules are strongly fluorescent, Raman microscopy is used to measure the vibration levels of intrinsic molecules in biological tissue, solid phase materials or on surfaces. In a Raman scattering process, a laser photon of a defined and stable wavelength is scattered from a molecule and shifted in wavelength by the vibrational energy level of a particular molecular bond. Raman spectroscopy and Raman microscopy typically operates with incident (excitation) light in the ultraviolet, visible or near infrared spectral regions which are weakly absorbed in many solvents such as water.

Conventional Raman microscopy has several drawbacks that have limited its application in biological imaging and hyper-resolution imaging, with hyper-resolution imaging defined as imaging with a resolution exceeding the diffraction limit. These include the following: 1) The incident laser light can stimulate fluorescent emission in the molecules under study, the solvent, or tissue under study which can coincide with the Stokes shifted Raman spectrum. 2) In general, the Raman process is inefficient. The collection efficiency of Raman scattered photons may be approximately $10^{-12}$. Since high intensity radiation of samples is limited by laser heating, Raman imaging and spectroscopy is a very slow process. 3) The scattering is non-directional, requiring very short working distances or very high numerical aperture lenses and microscope objectives. 4) Spectra of complex organic molecules may overlap, making it difficult to discriminate between different types of molecules. 5) Resolution is limited to that of the microscope which in general may be 0.4 microns or larger. 6) In small focal spots there are fewer molecules to produce the weak Raman scattering signal. 7) Poor scattering efficiency coupled with poor discrimination of signal and background makes detection of low concentrations of molecules impossible. 8) Raman transitions have very short excited state lifetimes. Virtual states for non-resonant Raman have femtosecond lifetimes, while Resonant Raman transitions have lifetimes in the 100 femtosecond range. These fast excited state decays make it impossible to use STED imaging techniques to achieve hyper-resolution imaging.

Variations of Raman imaging exist that can overcome several, but not all, of these deficiencies. For example, a longer excitation wavelength can be used to reduce background fluorescence; however, the molecular scattering cross section decreases with the inverse fourth power of the incident wavelength and the resolution in the image decreases with longer wavelength imaging. Alternatively, using resonant Raman spectroscopy can increase the Raman scattering cross section to $10^{-4}$ efficiency, whoever at the expense of significant enhanced fluorescent emission, and in tissues this is limited by the very strong background absorption in the ultraviolet (UV). The use of short laser pulses and time-gating the spectral acquisition to the sub-nanosecond regime may alleviate the adverse effects caused by fluorescence emission. However, most molecules have resonant absorption in the UV region which limits the use in plastic containers or the ability to see below the surface of biological tissues. Furthermore UV light often causes significant damage to biological and plastic materials, limiting its use to thin or surface samples.

A Raman technique that overcomes many of the aforementioned deficiencies is referred to as Coherent Anti-Stokes Raman Spectroscopy (CARS). CARS is a four-wave mixing process involving the generation of coherent vibration in the probed medium. Disadvantageously, the traditional CARS process produces a non-resonant incoherent background which can mask the measurement signal. This background is often caused by transitions involving solvent virtual levels. In addition, because the laser photons have to be tuned to the molecular transitions of interest, two or more different tunable picosecond lasers may be required. CARS also lacks adequate sensitivity, has a resolution of only about 300-400 nm, and cannot distinguish overlapping Raman bands.

Recently, Stimulated Raman Scattering (SRS) microscopy has demonstrated enhanced sensitivity over classical Raman microscopy, and similar Stimulated emission techniques have been shown to enhance the sensitivity of imaging with poorly fluorescent materials. These techniques rely on Stimulated emission of a traveling wave field to enhance the emission of light into the forward propagating laser field. This is the same process that produces "gain" in a laser beam propagating in a laser amplifier. However the femtosecond to picosecond lifetime of the excited states of these molecules have limited the application of STED techniques for use with these techniques for hyper resolution imaging.

When imaging biological cells and semiconductor devices, many of the structures of interest, such as chromosomes, ribosomes, membranes and transistor gates with dimensions below 100 nm, cannot be resolved with stimulated Raman and CARS microscopes.

It would therefore be desirable to provide an optical technique having an imaging resolution of better than 40 nm, for example, about 20-40 nm, with a high sensitivity and concurrent spectroscopic analysis. It would also be desirable to be able to image deeply below the surface which is not possible with resonance Raman techniques operating in the UV.

SUMMARY OF THE INVENTION

The systems and methods described herein make use of Stimulated Raman Scattering (SRS) to produce image resolution of a microscope beyond the diffraction limit.

According to one aspect of the invention, a laser scanning microscope includes a first light source producing monochromatic coherent pump light pulses having a first wavelength and a Gaussian beam profile, a second light source producing monochromatic coherent light pulses having a second wavelength and a Gaussian beam profile, a third light source producing monochromatic coherent light pulses having a third wavelength and an annular beam profile, and an optical assembly combining the light pulses from the first, second and third light sources into a pulsed overlapping light beam and focusing the overlapping light beam at a focal spot in a focal plane. The laser scanning microscope further includes a wavelength-dispersive detector receiving radiation produced responsive to the overlapping light beam in the focal plane, wherein the wavelength-dispersive detector is configured for detection of spectrally resolved received radiation of at least the first, second and third wavelengths.

According to another aspect of the invention, a method for stimulated fluorescence or Raman microscopy having resolution exceeding a diffraction limit includes the steps of producing monochromatic coherent pump light pulses having a first wavelength and a Gaussian beam profile, producing monochromatic coherent light pulses having a second wavelength and a Gaussian beam profile, producing monochromatic coherent light pulses having a third wavelength and an annular beam profile, combining the light pulses from the first, second and third light sources into a pulsed overlapping light beam and focusing the overlapping light beam at a focal spot in a focal plane, and spectrally-resolved detecting radiation produced responsive to the overlapping light beam in the focal plane.

Embodiments according to the invention may include one or more of the following features. The laser scanning microscope may include a microscope stage arranged substantially at the focal plane and configured to receive a sample receiving the overlapping light beam, wherein the microscope stage may be configured for displacement parallel to the focal plane so as to produce a two dimensional image of the sample by scanning the focal spot across the sample. The wavelength-dispersive detector may include a grating spectrometer. The coherent light pulses from the second light source and the coherent light pulses from the third source may arrive in the focal plane with an approximately zero phase shift or with a 180° phase shift between temporal centers of the coherent light pulses from the second and third light source. Alternatively, the phase shift between temporal centers of each of the coherent light pulses from the second and third light source may be random.

The second wavelength and the third wavelength may be adjusted to be sufficiently close so as to have a defined phase relationship during at least a portion of the pulse duration and to maintain destructive or constructive interference for at least half the temporal width or duration of the coherent light pulses.

According to some embodiments, the temporal width of the coherent pump light pulses may be smaller, for example between 30% and 500% smaller, than the temporal width of the coherent light pulses from the second light source as well as the temporal width of the coherent light pulses from the third source. The light pulses from the third source may be split into two beams which may be recombined in the focal plane to produce an interference pattern.

According to some embodiments, the annular beam profile may have an intensity of approximately zero at a location in the focal plane where the Gaussian beam from the first light source has maximum intensity. The annular beam profile at the third wavelength may have a peak intensity in the focal plane that is between approximately two and ten times, preferably between approximately three and five times, the peak intensity in the focal plane of the Gaussian beam at the second wavelength.

Further features and advantages of the present invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIG. 3 shows a photon detection spectroscopy system used to collect signals with GASSE microscopy;

FIG. 4 shows an intensity distribution (a); an energy level diagram of the three laser pulses (b); and an energy difference of the Stokes pulses in the homogenous transition bandwidth of the emission transition (c);

DETAILED DESCRIPTION OF EXEMPLARY EMBODIMENTS

Figure 1:
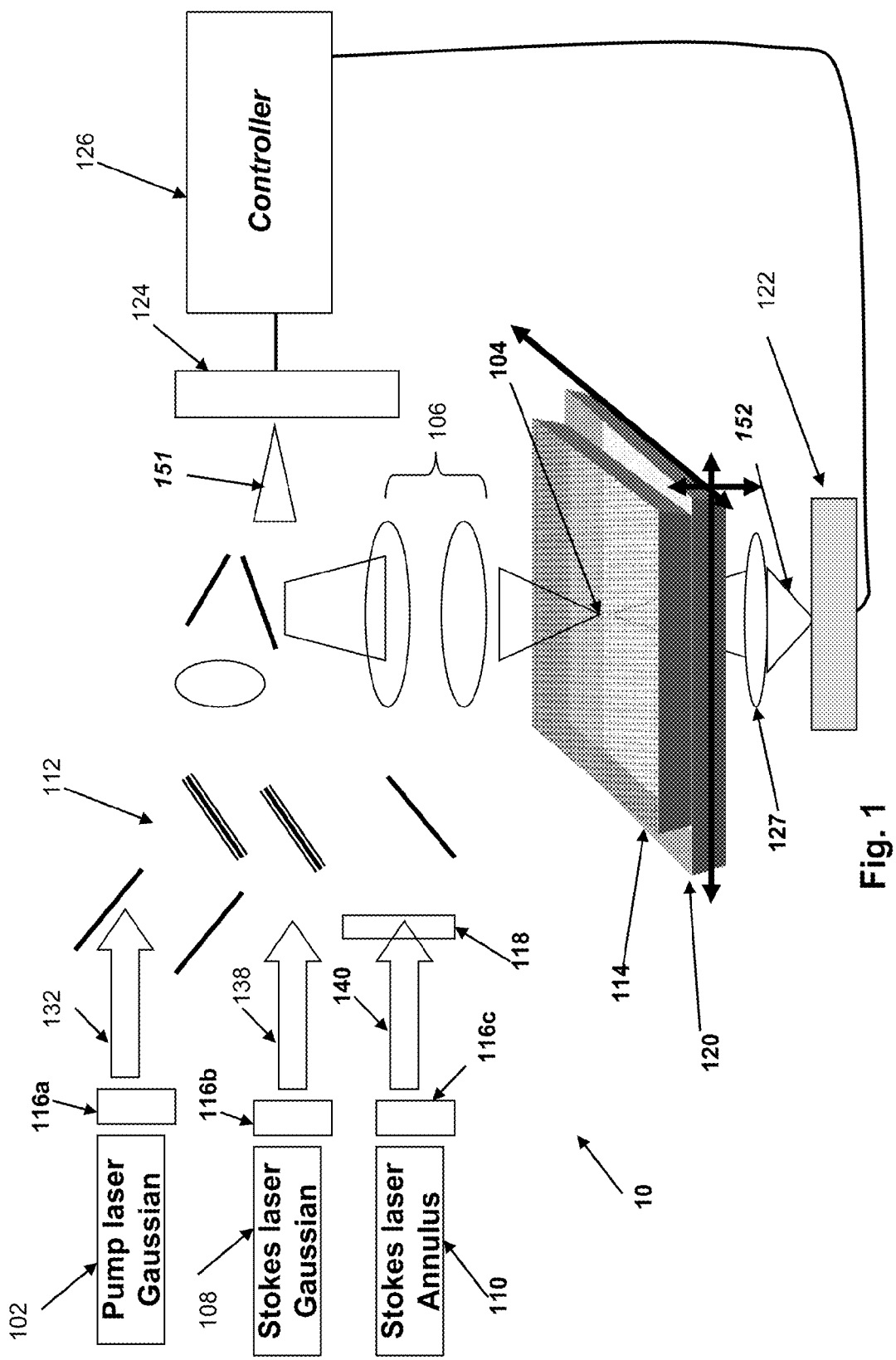
FIG. 1 shows schematically a system for scanning Gain Saturated Stimulated Emission (GASSE) microscope.

Referring now to FIG. 1, a microscopy system 10 focuses a pump beam 132 from a pump laser 102 emitting laser pulses with a Gaussian beam profile and picosecond duration in a diffraction limited spot 104 in the focal plane of a high numerical aperture (NA) microscope objective 106. A sample 114 to be investigated is located in or near the focal plane. The laser pulse 132 is used to pump the excited state that will emit stimulated emission. Picosecond laser pulses 138, 140 from two additional lasers 108, 110 that are at Stokes-shifted from the wavelength of the pump laser 102 are also focused at the diffraction limited spot 104. The pulses 138 and 140 from these lasers are referred to as "Stokes" pulses and are used to excite stimulated emission from the excited states of the sample. The energy differences between the pump and the Stokes pulses are within the stimulated emission bandwidth of the sample under study. The picosecond laser pulses 138 and 140 are either emitted so as to arrive at the focal spot 104 simultaneously with the pump beam 132, or with a slight time delay of several tens to hundreds of femtoseconds. Time delays enable vibrational excited states to relax to the lowest excited state energy level. This relaxation process differentiates fluorescent emission from Resonance Raman emission which occurs from the vibrational level that is directly excited. The delay may be introduced, for example, by placing an optical delay line with movable mirrors in the laser beams 138 and 140. The laser beams 138 and de-excite of the excited state via stimulated emission into vibrational excited states of the ground state manifold of energy levels of the excited molecule, as will be described below in more detail. The pump laser beam 132 and the two Stokes laser beams 138, 140 are combined by a optical assembly 112 which includes beam-combining optics, such as reflective and dichroic mirrors, beam splitters and lenses, commonly referred to by the reference symbol 112.

The two Stokes beams 138, 140 have specific characteristic wave fronts that enable imaging beyond the diffraction limit. In the illustrated example, the Stokes laser beam 140 has an annular intensity profile shape, for example, in the form of a torus of intensity with substantially zero in intensity at the center of the focal point of the pump beam in the focal plane. The inner surface of the torus may be modeled to have the shape of a parabola of revolution around the center of the microscope focus. This beam shape is introduced into the focus by a π-phase-shifting plate 118. In an alternative embodiment, the plate 118 may be replaced with a beam splitter configured to split the output of laser beam 140 into two beams which are then recombined at the focal spot 104 to produce a sine wave interference pattern enabling higher resolution in a one-dimensional scan. The other Stokes beam laser 138 has a Gaussian intensity profile and overlays the pump laser beam.

The system 10 can be used for virtual level resonance, one-photon and two-photon excitation or three-photon excitation GASSE applications. Resonance Raman applications may require Quartz optics that is transparent into the deep UV (DUV), possibly down to 240-190 nm. The lasers should emit picosecond or sub-picosecond pulses. The lasers may be three separate lasers, or may be seeded from one or two broad bandwidth lasers and separate spectral regions of a single pulse used to define the smaller bandwidth separate pulses, and should be tunable to stimulate different Raman or fluorescent resonances. The laser may be a tunable Ti:Sapphire laser, or a fiber laser with a continuum-generating fiber attached allowing spectral selection. The Ti:Sapphire laser may be configured as a parametric amplifier to produce the two laser frequencies required.

Figure 2:
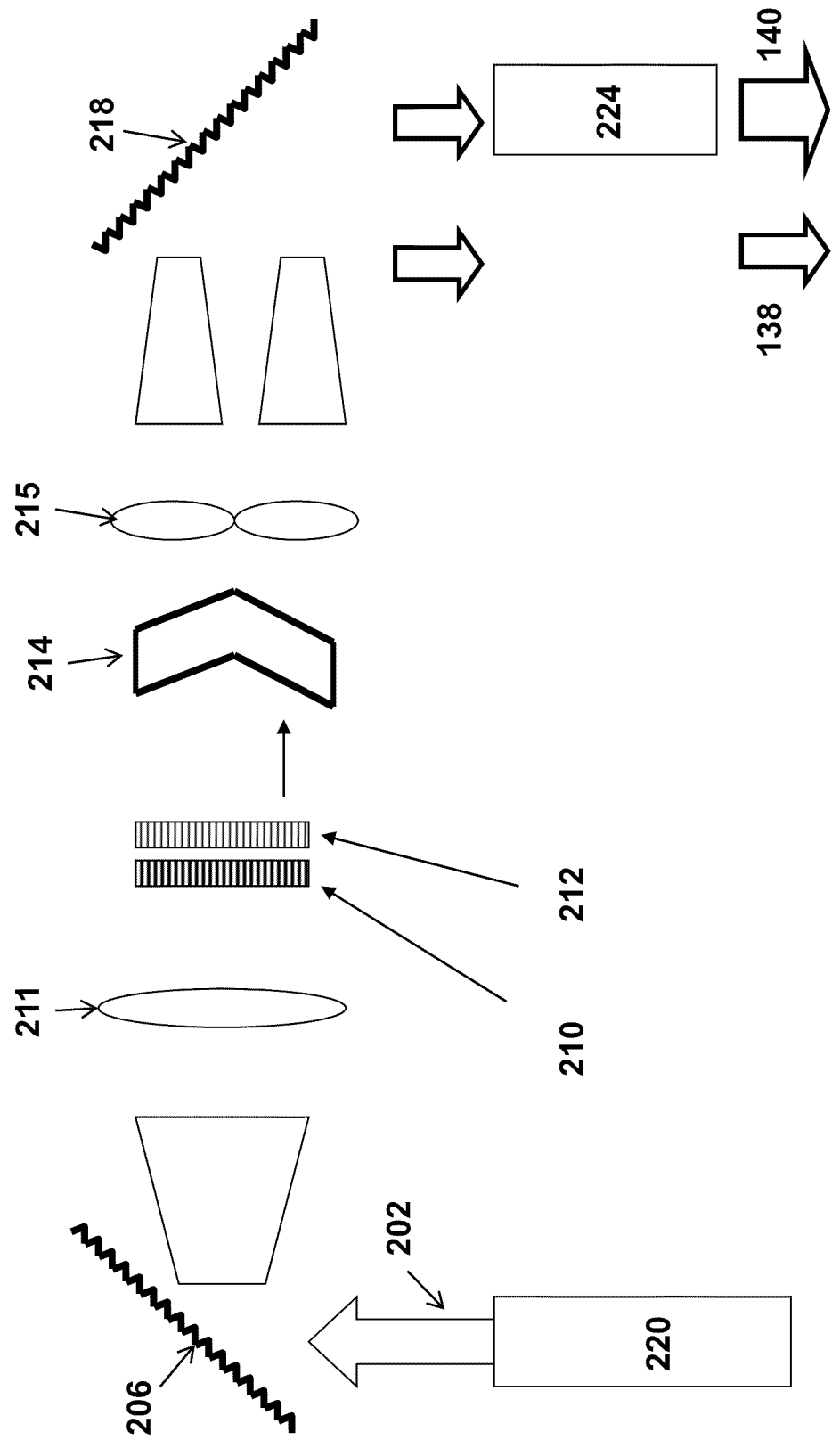
FIG. 2 shows a method of generating two Stokes pulses that are close together in wavelength and have a controlled phase and amplitude difference.

It is important that laser beams 138 and 140 have a controlled phase relationship and amplitude relationship between each other. In addition, it is important that they are very close together in wavelength as their central wavelength must be separated by less than the homogenous bandwidth of the stimulated emission levels. That is, the central wavelengths should be separated by less than 0.1-0.5 nanometers. FIG. 2 shows one exemplary method of generating these two beams from a single picosecond seed laser, such as a Ti:Sapphire solid state laser 220. The output beam 202 of laser 220 is spectrally dispersed by diffraction grating 206. The spectrally dispersed beam is collimated by lens 211. The phase of the frequency components of the beams may be changed by a first liquid crystal array 210 and the polarization may be altered by a second liquid crystal array 211. This is similar to the arrangement used in picosecond laser quantum phase control laser chemistry experiments. The spectral components of each of the two Stokes pulses may then be spatially separated by tilted plates 214. The two beams are then refocused by lens 215 and the spectral components of each beam are then recombined by grating 218. Laser amplifier 224 may then amplify Stokes beam 140 which should be 7-15 times more intense than laser beam 138. Laser beams 138 and 140 may then be frequency doubled or tripled as required for the application.

For UV resonance Raman and Fluorescence applications, frequency doubled, tripled, or quadrupled solid state lasers may be required. The wavelength separation of the two Stokes lasers may be defined by the homogeneous bandwidth of the Raman or fluorescent levels being probed. For two-photon pumping and two-photon stimulated emission the difference in the frequencies of the lasers correspond to half the vibration energy of the vibrational level being populated. When single-photon stimulated emission is used, the sum of the energy of the 1 or two-photon excitation minus the energy of the one photon stimulated emission photon should equal to the vibrational energy level.

The stimulated emission pulses must arrive simultaneously or within a few picoseconds of the excitation pulse as well as with a correctly defined phase relationship between the Stokes pulses in iGASSE systems. FIG. 1 shows conventional phase modulators 116a, 116b, 116c, such as liquid crystals and solid state modulators, disposed in each laser beam 132, 138, and 140.

The laser beams are combined by a beam splitter, overlapped in time and directed through a high NA microscope and focused on the sample. One of the Stokes beams has a phase shifting plate 118 to create an annular focus. Alternatively, a sine wave structured illumination may be produced by splitting the surround stokes beam in two beams and creating high NA off-axis inteferometric illumination, as used in structured illumination microscopic systems or inteferometric lithography imaging systems. For some applications, the sample may be mounted on a scanning microscope stage 120. For some applications a scanning stage may not be required.

The resonance back-reflected stimulated emission signal 151 and forward scattered stimulated emission gain signal 152 may be detected suitable spectrometers 122, 124 or filtered photo detector. The photons produced from annular and central stimulated emission should be separated. The imaging signal corresponds to the gain in intensity of the central Stokes beam 138, computed as the difference between the pumped and the unpumped (pump beam 132 turned off) intensity in beam 138. The gain in the annular stokes beam is not the image signal. Standard interference filters may not be adequate to separate these photons because they are close in wavelength and within the stimulated emission bandwidth of an electronic transition.

The spectrometers 122, 124 may be implemented as a conventional grating spectrometer 30, as shown in more detail in FIG. 3. The grating spectrometer 30, in this example spectrometer 122 of FIG. 1, receives light through an optical fiber 301 from, for example, condenser 127 (see FIG. 1). The optical fiber 301 may be a multimode fiber or a single mode fiber. Multimode fibers have cores larger than 50 microns or more and hence will collect more light. Alternatively, free space optics may be used instead of an optical fiber. The light may also be detected in the backward scattered direction by the "epi" light detection system 124, using a grating spectrometer 30 constructed in a similar manner. Epi scattering may be caused by multiple scattering beyond the focus of the laser, which may occur in thick samples, or by the small backscattered radiation component. The pump beam 132 and both Stokes gain pulses pass through condenser 127 and are recorded. The spectrometer may be positioned remote or integrated in the system 10. The light detection system of the spectrometer 30 may include silicon avalanche photodiodes 312, preferably fast photodiodes, or photomultiplier tubes. Stimulated emission photons are predominantly emitted in the forward direction of the stimulating beam laser modes. Gating the detector is typically used to eliminate background slower to appear fluorescence. The detection systems 122, 124 may be controlled by controller 126.

FIG. 3 shows a signal collection optical fiber 301 that receives light from condenser 127. The output of the fiber is collimated and passes through pump optical filter 303 to remove the excitation pump light. This filter may be a multilayer filter as used in Raman spectroscopy to remove excitation light. The light is then focused through the slit entrance 304 to a grating spectrometer, the grating 306 spectrally disperses and separates the stimulated emission enhanced central Stokes beam 338 and annular 340 Stokes beam. These beams are then focused by lens 304 on to an array of fast detectors 312. The controller 126 controls signal acquisition and computes the image. The signal for each image pixel is the difference between the central Stokes beam with the pump beam turned on to excite the sample and with the pump beam turned off. This is the "gain" in the stimulated emission from the focus of the central Stokes beam 338.

A diagrammatic representation of the GASSE process and electric field distributions at the focal point 104 for the three laser beams 132, 138, 140 are shown in FIG. 4a. The pump pulse 132 from laser 102 and the Stokes pulse 138 from laser 108 are focused to about the same diffraction limited focal spot diameter. Stokes pulse 138a is phase-shifted from Stokes pulse 138 by 180°. The pump pulse has a higher optical frequency than the Stokes pulses and thus will beat with the Stokes pulses if they have identical polarization and overlap in time. The other Stokes pulse 140 from laser 110 has an intensity distribution in the shape of an annulus because of the use of π-phase change wave plate 118. As mentioned above, laser beam 140 may in some cases be split by a beam splitter and recombined to interfere at the focal spot 104. In this case, the Stokes pulse 140 may have a sinusoidal energy distribution in one direction. This geometry may enable higher resolution in the direction perpendicular to the sinusoidal fringes; however, the resolution along the sine wave optical fringes is reduced. It may then become necessary to acquire the sample image from multiple directions to reconstruct the signal, as is done in computed tomography.

FIG. 4c shows the two Stokes pulses together with the Raman transition in the frequency domain. The wavelengths of the two Stokes pulses are generally very close to one another and may fall within the homogeneous bandwidth of Raman or fluorescent transition 405. For Raman transitions of molecules in solution, this bandwidth may be 5-25 cm$^{-1}$. As indicated by the dashed lines in FIG. 4a, the two Stokes pulses 138, 138a may have a phase difference of 180° and destructively interfere with one another at their positions of overlap as well as all other phase relations as constructively interfere by being in phase as is also shown. This destructive interference can advantageously be used in an interference GASSE (iGASSE) system to increase the optical resolution, as will be discussed below. As shown in the energy level diagram of FIG. 4b, the optical frequency of two Stokes beams may be close enough to cause stimulated emission into the same vibrational excited level in the ground state manifold of energy levels. This three level system enables the generation of a population inversion.

The following discussion will provide an overview of the stimulated emission characteristics of three regions within the microscope focal spot—the center, the middle region where the intensity of both Stokes pulses are significant and the region of high annular intensity. Near the center, the annular Stokes pulse has close to zero intensity. Therefore, stimulated emission into the central Stokes mode will occur, while no stimulated emission occurs into the annular beam. The stimulated emission from the central Gaussian is the signal that defines the resolution of the microscope 10. In the center region, the Gaussian and Annular Stokes beams may have different phase relationships with one another, as discussed in more detail below. No stimulated emission into either the central or annular fields will occur in this region when the two Stokes pulses have equal amplitude, but are 180° out of phase and hence interfere destructively. If the center Stokes and annular Stokes beams are in phase, stimulated emission may occur into both Stokes modes. Still farther away from the center of the focal point 104, the optical field of the annular Stokes mode will dominate and emission will occur primarily into the annular Stokes mode. It should be noted that as the pump pulse is Gaussian, there will be much fewer excited molecules to contribute to stimulate emission from the annular mode at the edge.

Stimulated emission will occur when a population inversion is produced between lower vibrational excited ground state vibrational energy level $N_0^*$ and excited state level $N_1$, as shown in the energy level diagram of FIG. 4b. The difference between fluorescent emission and Raman emission, is also illustrated in FIG. 4b. In an example of Raman emission, pump beam 132 excites the specific level $N_1$ that emits radiation. In the illustration, the emission level is the lowest energy level, but it could be a higher excited state like $N_1^*$. Fluorescent emission occurs from the lowest excited $N_1$. The pump beam may excite higher level $N_1^*$, however some of the excitation energy is dissipated by collisions, phonons or radiation and electrons collect into state $N_1$. This loss of energy is called the Kasha process. The Kasha process occurs on a time scale of tens to hundreds of femtoseconds. In molecules with long fluorescent lifetime and high efficiency the excited state $N_1$ may last for tens to hundreds of nanoseconds.

Gain saturation occurs when the population of the lower excited ground state and excited state of an electron transition in a medium are equal, by preventing stimulated emission because the probability of addition or subtraction from the stimulated traveling wave field is equal. A key function of the annular Stokes field is to drive the homogenously broadened molecular transition, at the positions of overlap with the central field, toward a population distribution of 50/50 between the upper and lower energy levels. As the annular field becomes more intense, both the spatial position of gain saturation and the width of the central Stokes stimulated Point Spread Function(PSF) move toward the center of the Gaussian focal spot. Gain saturation produces the narrowing of the region of stimulated emission gain into laser beam 308 and the results is hyper-resolution stimulated emission imaging.

The in-phase and out-of-phase Stokes pulse GASSE systems operate differently. In Maxwell's Equations the only radiation interaction term is defined in relationship to the polarizabilty of the medium. Physically, the higher the intensity of the field, the higher the polarization of the medium produced by the beam and the higher the probability of stimulated emission. If the two Stokes fields from laser beams 138 and 140 are well below saturation and are in-phase and add constructively, then they work together to enhance the polarization of the medium and the oscillation of the elections to be in phase with the stimulated emission modes. If one field is significantly more intense than the other, then the probability of emission into that field will be much greater than into the other. As the field of the strong field summed with the weaker field drives the emitters into saturation, there will be no gain in either field since the transition is homogeneous. This means that there is nothing to constrain the emitters from sampling the entire homogenous bandwidth driven by local field variations, vibrational interactions, or other thermal driven effects. The sum of the strong and weak fields drives the medium into saturation at intensities for each field that are less than would drive the medium into saturation for one field. The stronger annular field, the closer to the center the region of gain saturation becomes and hence the region of central gain is narrowed.

When the Stokes fields destructively interfere, they do not act cooperatively to increase the polarization of the medium. The polarization of the medium will be controlled by the stronger field and will move the transition into saturation and completely eliminating the gain in the weak out-of-phase field. The electrons in the excited molecules cannot resonant with the weaker out-of-phase field. Thus the hyper-resolution is improved when the Stokes fields are out of phase.

Figure 5:
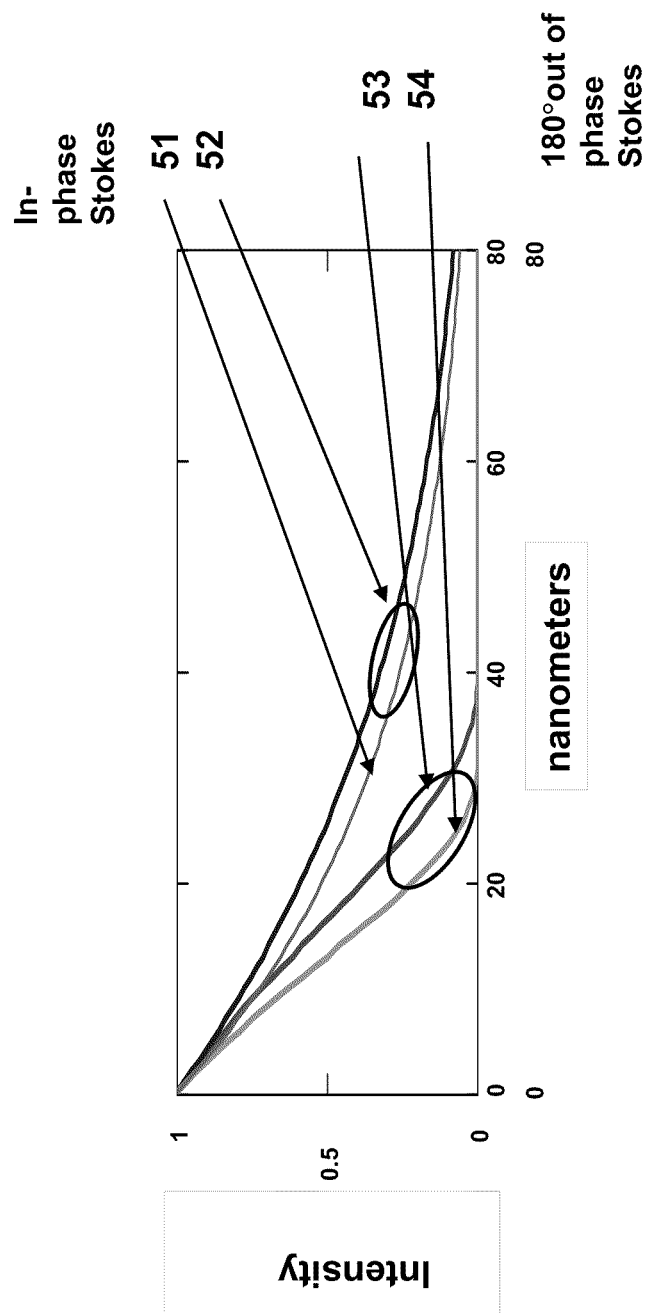
FIG. 5 shows a diagram depicting resolution enhancement of an inteferometric GASSE (iGASSE) microscope with the Stokes pulses in-phase and 180 degrees out of phase.

FIG. 5 compares Point Spread Functions (PSF) of in-phase 51, 52 and 180° out-of-phase iGASSE systems 53, 54 operating at Stokes wavelengths of 803.6 nm and 804 nm with a microscope objective having a Numerical Aperture (NA) of 1.4. These calculations assume that a confocal Point Spread Function PSF of the central excitation is a Gaussian $h_{cf}(x) \approx \exp(-4\ln 2\, (x)^2/d_{cf}^2)$, wherein $d_{cf} = \lambda_{sc}/(2NA)$. The variable x is the distance for the center of focal spot, $\lambda_{sc}$ is the wavelength of the central Stokes beam and $d_{cf}$ is the Full Width at Half Maximum (FWHM) of the confocal microscope in terms of the microscope NA. The Stokes annular intensity is modeled as a parabola with a steepness p. The intensity of the parabola is defined $I(x) = 4I_{AsTM}p^2x^2$, where $I_{ASTIM}$ is the maximum intensity of the annulus. In FIG. 5 the intensity is normalized to the peak intensity of the central Stokes beam. This intensity of the central Stokes beam produces linear stimulated emission gain at its center. The curves 51 and 52 are for in-phase Stokes illumination with the maximum annular illumination of 10 and 6 times a normalized saturation value. Curves 53 and 54 are PSFs of iGASSE systems having normalized maximum parabolic intensities of 10 and 6 times saturation for the transition.

In all cases, the FWHM of the PSFs (the value at 2 times the x on the plots when I=0.5 on the y axis) of the system are under 60 μm. The smallest PSF is about 30 nm which is a factor 10 less than a standard stimulated emission microscope at this wavelength and NA. Destructive interference improves the hyper resolution by about 40% and the off-axis tail in the PSF is reduced, compared to the in-phase PSFs. The conclusion is that destructive interference coupled with gain saturation is more effective in producing enhanced resolution than straight gain saturation with the Stokes fields in phase. If the phase relationship is randomized and the fields are not coherent with relation to each other, the resolution enhancement will be between the in-phase and out-of-phase systems.

Figures 6A, 6B:
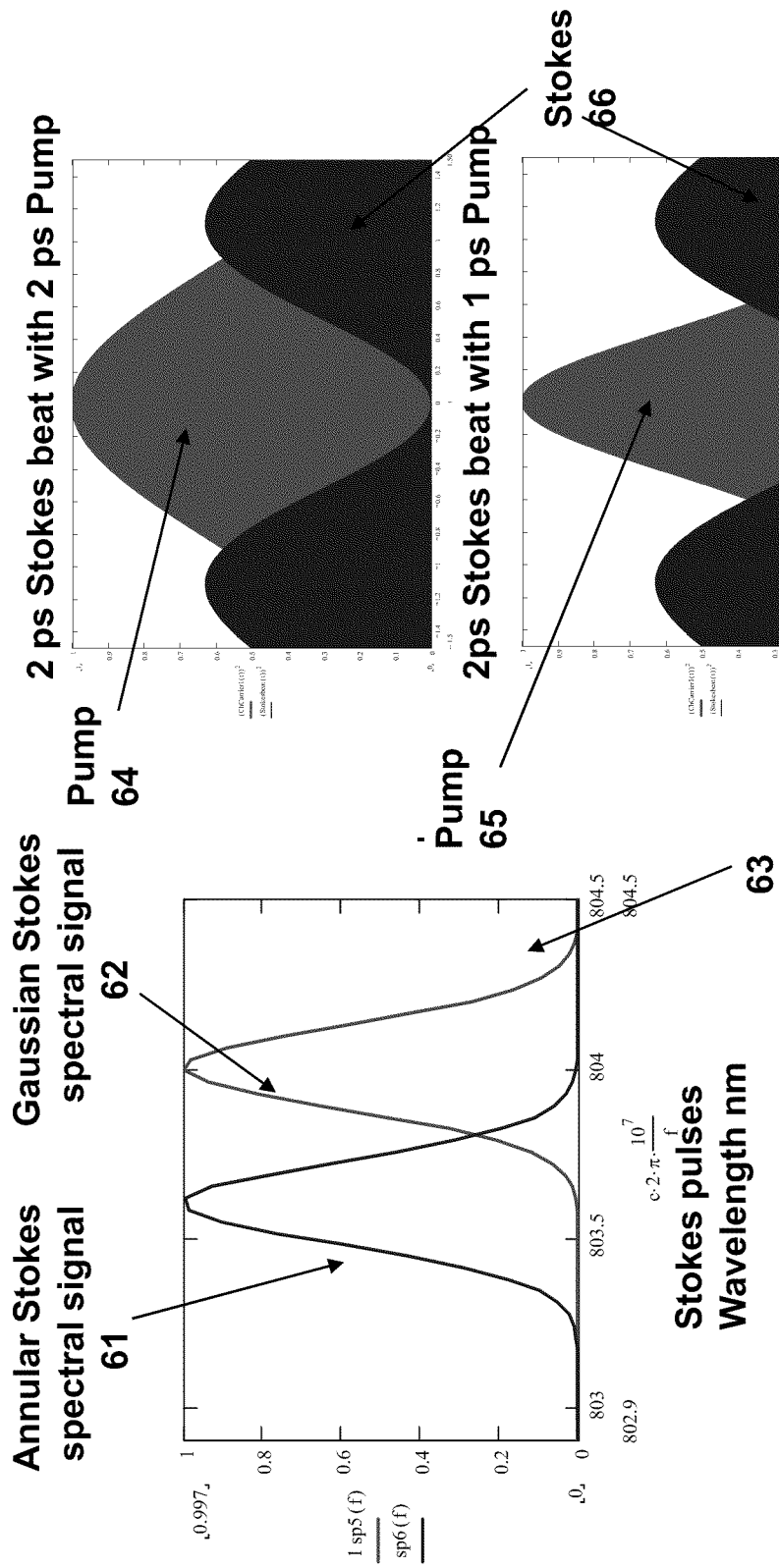
FIG. 6 shows the intensity and beat intensity of two interfering 750 fs Stokes pulses and the bandwidth of each pulse.

It is therefore desirable to have spectrally separate Stokes pulses with a 180° phase shift for maximum resolution enhancement. Although it is difficult to spectrally separate and temporally phase-match the two Stokes pulses over their entire pulse width, phase-matching may be attained over a shorter pump pulse duration, as shown in FIGS. 6*a*-*b*. FIG. 6*a* shows the spectra of two Stokes pulses each having duration (FWHM) of 2 picoseconds. The annular Stokes pulse 61 has a spectral peak at 803.6 nm, while the central Stokes pulse 62 has a spectral peak at 804.0 nm. The spectral components of the two pulses are substantially separated, but there is some small spectral overlap. Curve 66 in FIG. 6*b* shows the intensity of the beating Stokes pulses (having Gaussian pulse shapes) of FIG. 6*a* plotted as a function of time, with the phases being 180° out-of-phase at the temporal center of these pulses. The beat frequency plot is taken at the spatial position at the focal spot where the intensities of the annular and Gaussian Stokes pulses are equal. It is evident that the leading and trailing edges of the pulse move into phase, while interference is complete at the peak of the pulses. Effects caused by the leading and trailing edges can be minimized if the central pump pulse from beam 132 is of a shorter duration than the Stokes pulses from beams 138, 140. Curve 65 in FIG. 6*b* shows the envelope of a one picosecond pump pulse, and curve 66 in FIG. 6*b* shows the envelope of a two picosecond pump pulse. As can be seen from FIG. 6*b*, a narrower pump pulse can minimize the time when the emitters are in an excited state and the Stokes pulses are in phase. This strategy will work well for Stimulated Resonance Raman imaging, where the pump and Stokes pulses would arrive at the focus simultaneously. However, a different temporal relationship between the pump and Stokes pulses may be desirable for fluorescent imaging, where the pump pulse may be delayed relative to the Stokes pulse to allow population buildup in the lowest excited state level.

The constructive interference at the trailing edge may be minimized by time-gating the detector or frequency-shifting the stimulated emission pulse through a non-linear crystal to pick out the central time window of the pulse.

Figure 7:
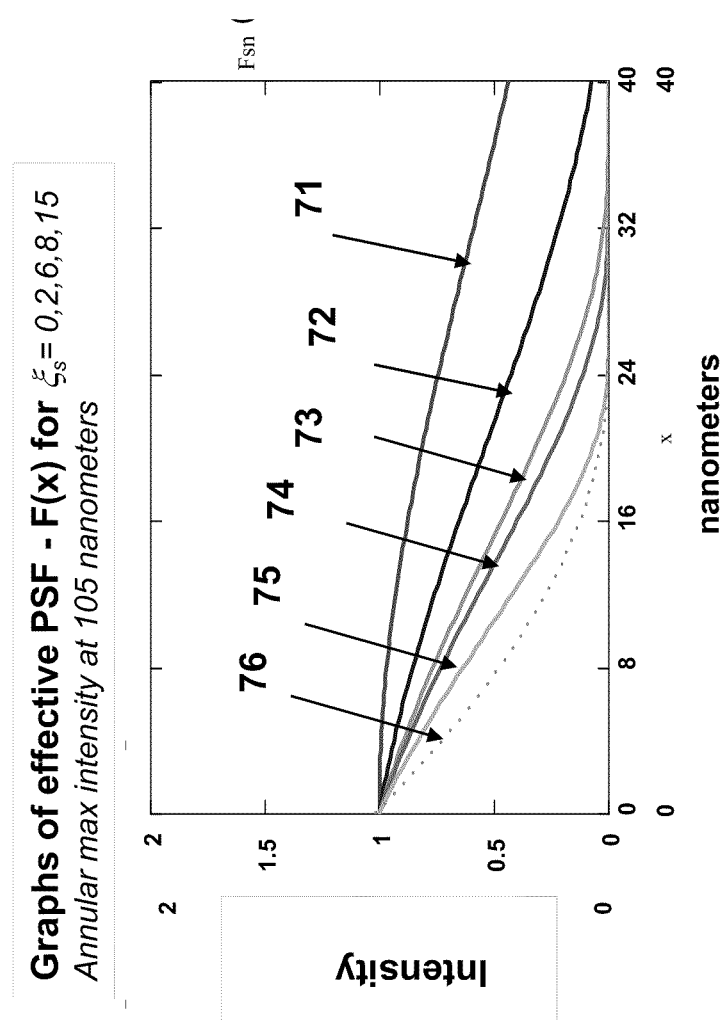
FIG. 7 shows a diagram depicting resolution enhancement of an iGASSE microscope compared to a stimulated emission microscope.

FIG. 7 illustrates the point spread function of an iGASSE microscope operating with a Stokes beam in the ultraviolet (UV) region of the spectrum at a wavelength of about 200 nm. Plotted are the PSFs 72, 73, 74, 75, 76 of an UV iGASSE microscope having a numerical aperture NA=1.0 with water immersion and operating at 4 different annular intensities. The PSF 71 from a UV stimulated Raman emission microscope without a Stokes annular beam is shown for comparison. It is assumed the annulus has a parabolic intensity shape with an off-axis peak to peak distance of 210 microns. A parabolic approximation to the annular beam is the same assumption used in modeling the PSF of STED microscopy. It is assumed that the peak intensity of the central Gaussian pump and Stokes pulses are identical. The intensities of the parabolic annular pulses are normalized to the intensity of the peak intensity of the annular beam in units of saturation intensity of an emission transition. The PSFs 72, 73, 74, 75 are produced by pulses of 2, 6, 8 and 15 times, respectively, the saturation intensity of a synthetic transition at the off-axis peak of the parabolic Stokes pulse. The PSFs are plotted in a radial direction outward from the center of the Gaussian beam. The FWHM of the PSF of the stimulated Raman UV microscope 71 is about 74 nm. This is about 30% smaller than for a one-photon UV microscope due to the two photon nature of stimulated emission imaging. The iGASSE microscopes operating at 8 and 15 times the saturation value in the annulus have a FWHM of about 30 nm and 20 nm, respectively. These curves use a conservative assumption that the pump pulse and the central Stokes have identical Gaussian FWHM. However for a 1600 cm$^{-1}$ Raman transition, the pump pulse will be of shorter wavelength, and thus have a narrow Gaussian excited state distribution. If the excited state Gaussian is reduced to 70% of the Stokes Gaussian then the FWHM PSF of the iGASSE system with Stokes intensity of 15 is reduced to 16 nm, as shown in curve 76. If a sinusoidal Stokes pulse with an off-axis peak-to-peak separation of 100 nm is used instead of a parabolic illumination, the FWHM values of these PSFs will be reduced by over 50% to 16 and 12 nm, respectively. These plots are not shown.

Figure 8:
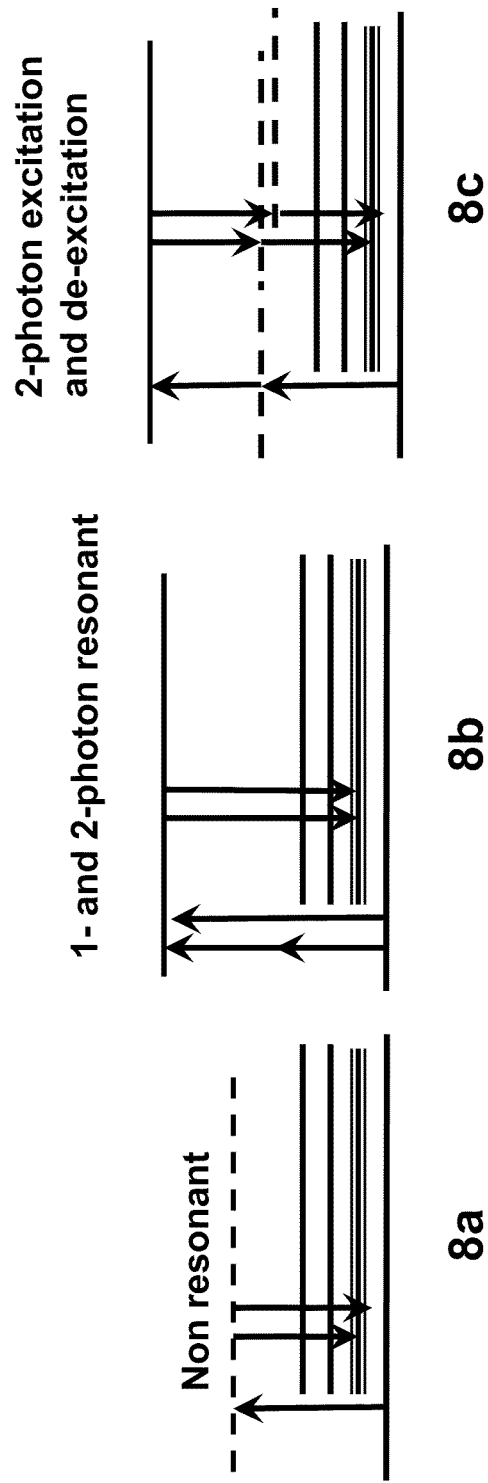
FIG. 8 shows single and multi-photon variations of GASSE microscopy.

GASSE microscopy may work with real and virtual electronic transitions. However the resolution enhancement achieved may be best with real transitions, which require lower electric field strength to approach saturation. FIG. 8 shows various electronic level transitions that may be considered to achieve GASSE hyper-resolution imaging. FIG. 8a shows the GASSE approach with a virtual transition. This approach has the advantage of using infrared illumination, as used in CARS imaging. Disadvantageously, saturation is difficult to maintain because the excited state lifetime is only in the femtosecond range. However, hyper-resolution can still be achieved with iGASSE systems because the higher mode occupation number in the annular Stokes field enhances the emission probability. FIG. 8b shows one-photon and two-photon excitation. Since many organic Raman and fluorescent transitions have absorption edges in the UV region of the spectrum between 200 and 300 nm, one-photon resonance excitation requires very thin specimens or tissue sections. two-photon excitation enables use of thicker sections or living cells for GASSE imaging. The disadvantage of two-photon stimulated emission is the requirement for high optical field because of the transition of the excitation through a virtual level of femtosecond duration. The emission light is red-shifted enabling better penetration of the tissue by the stimulated emission. FIG. 8c shows another variation of GASSE which uses two-photon excitation and three-photon stimulated emission. Although very intense excitation and stimulation fields are required, this process can advantageously achieve deep tissue or sample penetration due to the use of infrared photons which may be advantageous for in-vivo applications.

GASSE imaging may be used to image many various types of molecules and organelles at better than 30 nm resolution. Raman emission bands are defining for proteins, nucleic acids in RNA and DNA and for lipids. Also small drug molecules may be imaged with precise Raman scattering signals. Therefore ultra-high spatial resolution imaging disclosed in this application may enable imaging of DNA structures, ribosomes, actin filaments, and physiological concentrations of unlabelled small molecule drugs and the spatial relationship of these molecules without external labels. The structure and position of neurotransmitter enclosed vesicles and the base sequence motifs of nucleic acids may be explored with very high resolution. A resolution of better than 10 nm may be achieved with electron-resonance iGASSE at 260-340 nm and water immersion UV imaging. This is close to the length of one turn of a double helix of DNA and about 25 base pairs. Thus, the iGASSE microscope could be a replacement for electron microscopic imaging with similar resolution and no requirement for denaturing stains and with simultaneous molecular identity resolution.

Another application may be high-resolution mapping of tissue from ultra-thin sections to reveal, for example, the complete 3-dimensional connectivity of unstained or stained sections in the brain. The entire connection network of the brain is called the connectosome. Processing speed is significantly enhanced and sample preparation is simplified compared to electron microscopy.

The high resolution short-wavelength GASSE systems are expected to find applications in semiconductor manufacturing metrology, such as characterization of lithographic exposure, overlay accuracy between lithographic layers, metrology of molecular electronics devices made of nanotubes, nanowires, and grapheme layers, as well as biological research. For example, in advanced submicron devices strained Silicon (Si) and Silicon Germanium (SiGe) layers are used to enhance the device speed. These films are typically thin, and the high depth resolution of the invention defined here will allow depth resolution equal to the lateral resolution of the system. The high spatial resolution of the invention will allow direct high resolution mapping of temperature changes within a semiconductor wafer below the surface insulation layers. In addition, as device structures move to feature sizes of less than 20 nm, stress engineering at these device dimensions is of critical importance, in particular for compound semiconductors. GASSE imaging may be used to directly measure stress at the gates and/or interfaces.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the appended claims.

What is claimed is:

1. A laser scanning microscope comprising:
   a first light source producing monochromatic coherent pump light pulses having a first wavelength and a Gaussian beam profile;
   a second light source producing monochromatic coherent light pulses having a second wavelength and a Gaussian beam profile;
   a third light source producing monochromatic coherent light pulses having a third wavelength and an annular beam profile;
   an optical assembly combining the light pulses from the first, second and third light sources into a pulsed overlapping light beam and focusing the overlapping light beam at a focal spot in a focal plane;
   a wavelength-dispersive detector receiving radiation produced responsive to the overlapping light beam in the focal plane, said wavelength-dispersive detector configured for detection of spectrally resolved received radiation of at least the first, second and third wavelengths.

2. The laser scanning microscope of claim 1, further comprising a microscope stage arranged substantially at the focal plane and configured to receive a sample receiving the overlapping light beam.

3. The laser scanning microscope of claim 1, wherein the wavelength-dispersive detector comprises a grating spectrometer.

4. The laser scanning microscope of claim 1, wherein the coherent light pulses from the second light source and the coherent light pulses from the third source arrive in the focal plane with an approximately zero phase shift between temporal centers of the coherent light pulses from the second and third light source.

5. The laser scanning microscope of claim 1, wherein the coherent light pulses from the second light source and the coherent light pulses from the third light source arrive in the focal plane with a 180° phase shift between temporal centers of the coherent light pulses from the second and third light source.

6. The laser scanning microscope of claim 1, wherein the coherent light pulses from the second light source and the coherent light pulses from the third source arrive in the focal plane with a random phase shift between temporal centers of each of the coherent light pulses from the second and third light source.

7. The laser scanning microscope of claim 1, wherein a temporal width of the coherent pump light pulses is smaller than a temporal width of the coherent light pulses from the second light source and a temporal width of the coherent light pulses from the third source.

8. The laser scanning microscope of claim 7, wherein the temporal width of the coherent pump light pulses is at least 30% shorter than the temporal width of the coherent light pulses from the second light source and the temporal width of the coherent light pulses from the third source.

9. The laser scanning microscope of claim 8, wherein the temporal width of the coherent pump light pulses is at most 5 times shorter than the temporal width of the coherent light pulses from the second light source and the temporal width of the coherent light pulses from the third source.

10. The laser scanning microscope of claim 1, wherein the light pulses from the third source are split into two beams which are recombined in the focal plane to produce an interference pattern.

11. The laser scanning microscope of claim 1, wherein the annular beam profile has an intensity of approximately zero at a location in the focal plane where the Gaussian beam from the first light source has maximum intensity.

12. The laser scanning microscope of claim 1, wherein the annular beam profile at the third wavelength has a peak intensity in the focal plane that is between approximately two and ten times a peak intensity in the focal plane of the Gaussian beam at the second wavelength.

13. The laser scanning microscope of claim 12, wherein the annular beam profile at the third wavelength has a peak intensity in the focal plane that is between approximately three and five times a peak intensity in the focal plane of the Gaussian beam at the second wavelength.

14. The laser scanning microscope of claim 2, wherein the microscope stage is configured for displacement parallel to the focal plane so as to produce a two dimensional image of the sample by scanning the focal spot across the sample.

15. A method for stimulated fluorescence or Raman microscopy having resolution exceeding a diffraction limit, comprising the steps of:
  producing monochromatic coherent pump light pulses having a first wavelength and a Gaussian beam profile;
  producing monochromatic coherent light pulses having a second wavelength and a Gaussian beam profile;
  producing monochromatic coherent light pulses having a third wavelength and an annular beam profile;
  combining the light pulses from the first, second and third light sources into a pulsed overlapping light beam and focusing the overlapping light beam at a focal spot in a focal plane; and
  spectrally-resolved detecting radiation produced responsive to the overlapping light beam in the focal plane.

16. The method of claim 15, further comprising the step of adjusting an intensity of the coherent light pulses having the third wavelength to be greater than an intensity of the coherent light pulses having the second wavelength.

17. The method of claim 15, further comprising the step of adjusting the second wavelength and the third wavelength to be sufficiently close, so as to have a defined phase relationship during at least a portion of a pulse duration and to maintain destructive or constructive interference for at least half a temporal width of the coherent light pulses.

18. The method of claim 17, wherein destructive interference is produced by adjusting a phase shift between the light pulses having the second and third wavelengths to approximately 180°.

\* \* \* \* \*